(12) United States Patent
Charles

(10) Patent No.: US 10,172,516 B2
(45) Date of Patent: Jan. 8, 2019

(54) FOGGING PREVENTION FOR SURGICAL CONTACT LENSES

(71) Applicant: Novartis AG, Basel (CH)

(72) Inventor: Steven T. Charles, Germantown, TN (US)

(73) Assignee: Novartis AG, Basel (CH)

(*) Notice: Subject to any disclaimer, the term of this patent is extended or adjusted under 35 U.S.C. 154(b) by 70 days.

(21) Appl. No.: 15/499,581

(22) Filed: Apr. 27, 2017

(65) Prior Publication Data

US 2017/0319062 A1 Nov. 9, 2017

Related U.S. Application Data

(60) Provisional application No. 62/332,093, filed on May 5, 2016.

(51) Int. Cl.
| | | |
|---|---|---|
| *A61B 3/13* | (2006.01) | |
| *A61B 3/125* | (2006.01) | |
| *A61F 9/007* | (2006.01) | |
| *G02B 27/00* | (2006.01) | |
| *G02B 7/00* | (2006.01) | |
| *G02C 7/04* | (2006.01) | |

(52) U.S. Cl.
CPC ............... *A61B 3/13* (2013.01); *A61B 3/125* (2013.01); *A61F 9/007* (2013.01); *G02B 7/008* (2013.01); *G02B 27/0006* (2013.01); *G02C 7/049* (2013.01)

(58) Field of Classification Search
CPC ............ A61B 1/127; A61B 1/04; A61B 3/125; A61B 3/13
USPC .................... 351/219, 205, 246; 600/169
See application file for complete search history.

(56) References Cited

U.S. PATENT DOCUMENTS

| | | | |
|---|---|---|---|
| 4,056,310 A | 11/1977 | Shimizu et al. | |
| 8,597,179 B2 * | 12/2013 | Kokubo | A61B 1/05 600/109 |
| 2012/0034573 A1 | 2/2012 | Erdmann et al. | |
| 2013/0035672 A1 | 2/2013 | Raksi | |

FOREIGN PATENT DOCUMENTS

| | | |
|---|---|---|
| DE | 202011005230 U1 | 9/2011 |
| JP | 2014-124277 A | 7/2014 |
| WO | 97/31293 A1 | 8/1997 |

* cited by examiner

*Primary Examiner* — Hung Dang

(57) ABSTRACT

A contact lens for use with a surgical microscope may be equipped with an anti-fogging device to prevent obscuring the view of a surgeon due to condensation during ophthalmic surgery. The anti-fogging device may deliver thermal energy to a surface of the contact lens to heat the contact lens above an ambient dew point. The thermal energy may be delivered by an air duct with a fan nozzle, a fluid duct in thermodynamic contact with the contact lens circulating a heat transfer fluid, or generated with electrical energy to an electrical heating element disposed on the surface of the contact lens. The thermal or electrical energy may be delivered via a handle for supporting the contact lens during surgery.

20 Claims, 3 Drawing Sheets

FOGGING PREVENTION FOR SURGICAL CONTACT LENSES

BACKGROUND

Field of the Disclosure

The present disclosure relates to ophthalmic surgery, and more specifically, to fogging prevention for surgical contact lenses.

Description of the Related Art

In ophthalmology, eye surgery, or ophthalmic surgery, is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus. For many types of vitreoretinal surgery using the surgical microscope, the surgeon may desire to have a very wide field of view of the fundus that extends beyond the equator and even out to the or a serrata. The optical system to provide the view of the fundus to the surgeon during vitreoretinal surgery may include a special ocular lens, of which three types are typically used: a direct (piano, flat, or magnifying) contact lens, an indirect non-contact lens, or an indirect contact lens.

A contact lens is in physical contact with the cornea and therefore has a concave surface to match the convex surface of the cornea. Typically a small amount of gel or fluid resides between the cornea and the contact lens to prevent unwanted extraneous interfacial reflections and to protect the cornea from dehydration.

Because of the thermal mass of many contact lenses, such as those incorporating multiple internal objectives, high water vapor content of the air near the eye, and the ambient conditions in operating rooms, contact lenses may be subject to fogging during surgery, which is undesirable because the surgeon's view of the fundus is obstructed.

SUMMARY

The disclosed embodiments of the present disclosure provide fogging prevention for contact lenses used during ophthalmic surgery. The methods and systems for fogging prevention disclosed herein may include an anti-fogging device that delivers thermal energy to the contact lens during ophthalmic surgery. The methods and systems for fogging prevention disclosed herein may deliver thermal energy to heat the contact lens above an ambient dew point to prevent condensation (fogging) of the contact lens during surgery. The methods and systems for fogging prevention disclosed herein may enhance safety of ophthalmic surgery by preventing the view of the surgeon from being obscured by fogging of the contact lens during surgical procedures.

In one aspect, a disclosed method is for performing ophthalmic surgery. The method may include positioning a first optical axis of a surgical microscope along a second optical axis of an eye of a patient, and viewing an interior portion of the eye using a contact lens in contact with the eye. The method may also include activating an anti-fogging device coupled to the contact lens. In the method, the anti-fogging device may deliver thermal energy to the contact lens.

In any of the disclosed embodiments of the method, the anti-fogging device may include an air duct in fluid coupling to an air nozzle directed to a surface of the contact lens. In the method, the air duct may transport heated air towards the air nozzle to deliver the thermal energy. In any of the disclosed embodiments of the method, the air nozzle may be a fan beam nozzle.

In any of the disclosed embodiments of the method, the anti-fogging device may include an electrical heating element disposed on a surface of the contact lens to deliver the thermal energy. In the method, the electrical heating element may include a transparent conductor. In any of the disclosed embodiments of the method, the anti-fogging device may include an electrical heating element disposed on a ring surrounding the contact lens.

In any of the disclosed embodiments of the method, the anti-fogging device may include a fluid duct in thermodynamic contact with the contact lens. In the method, the fluid duct may circulate a heat transfer fluid to deliver the thermal energy. In the method, the heat transfer fluid may be an aqueous saline or a sterile water solution.

In any of the disclosed embodiments of the method, the anti-fogging device may further include a handle for supporting the contact lens on the eye during surgery.

In another aspect, a disclosed contact lens is for ophthalmic surgery. The contact lens may include an anti-fogging device coupled to the contact lens. In the contact lens, the anti-fogging device may delivers thermal energy to the contact lens while the contact lens is in use during ophthalmic surgery to view an interior portion of an eye of a patient using a surgical microscope.

In any of the disclosed embodiments of the contact lens, the anti-fogging device may include an air duct in fluid coupling to an air nozzle directed to a surface of the contact lens, while the air duct transports heated air towards the air nozzle to deliver the thermal energy. In the contact lens, the air nozzle may be a fan beam nozzle.

In any of the disclosed embodiments of the contact lens, the anti-fogging device may include an electrical heating element disposed on a surface of the contact lens to generate the thermal energy. In the contact lens, the electrical heating element may include a transparent conductor. In any of the disclosed embodiments of the contact lens, the anti-fogging device may include an electrical heating element disposed on a ring surrounding the contact lens.

In any of the disclosed embodiments of the contact lens, the anti-fogging device may include a fluid duct in thermodynamic contact with the contact lens, while the fluid duct may circulate a heat transfer fluid to deliver the thermal energy. In the contact lens, the heat transfer fluid may be an aqueous saline or a sterile water solution.

In any of the disclosed embodiments of the contact lens, the anti-fogging device may further include a handle for supporting the contact lens on the eye during surgery.

In any of the disclosed embodiments of the contact lens, the thermal energy may be delivered via the handle.

In any of the disclosed embodiments of the contact lens, electrical energy to generate the thermal energy may be delivered via lead lines attached to the handle.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

In the following description, details are set forth by way of example to facilitate discussion of the disclosed subject matter. It should be apparent to a person of ordinary skill in the field, however, that the disclosed embodiments are exemplary and not exhaustive of all possible embodiments.

As noted above, contact lenses, often comprised of multiple objectives, may have a relatively high thermal mass and may experience fogging during ophthalmic surgery. Typically in an operating room where ophthalmic surgery is being performed, the ambient conditions may include high humidity and cooling air from ventilation systems may be present. Thus, the contact lens may become cold, while local humidity near the surgical procedure, particularly around the eye, may be increased, which may result in condensation forming on the surface of the contact lens. Because such fogging may be unpredictable or spontaneous, the resulting loss of view of the fundus for the surgeon may impede the normal course of the surgical procedure being performed, which is undesirable.

As will be described in further detail, the inventors of the present disclosure have developed methods and systems for fogging prevention for surgical contact lenses. The methods and systems for fogging prevention disclosed herein may include an anti-fogging device that delivers thermal energy to the contact lens during ophthalmic surgery. The methods and systems for fogging prevention disclosed herein may deliver thermal energy to heat the contact lens above an ambient dew point to prevent condensation (fogging) of the contact lens during surgery. The methods and systems for fogging prevention disclosed herein may enhance safety of ophthalmic surgery by preventing the view of the surgeon from being obscured by fogging of the contact lens during surgical procedures.

Figure 1:
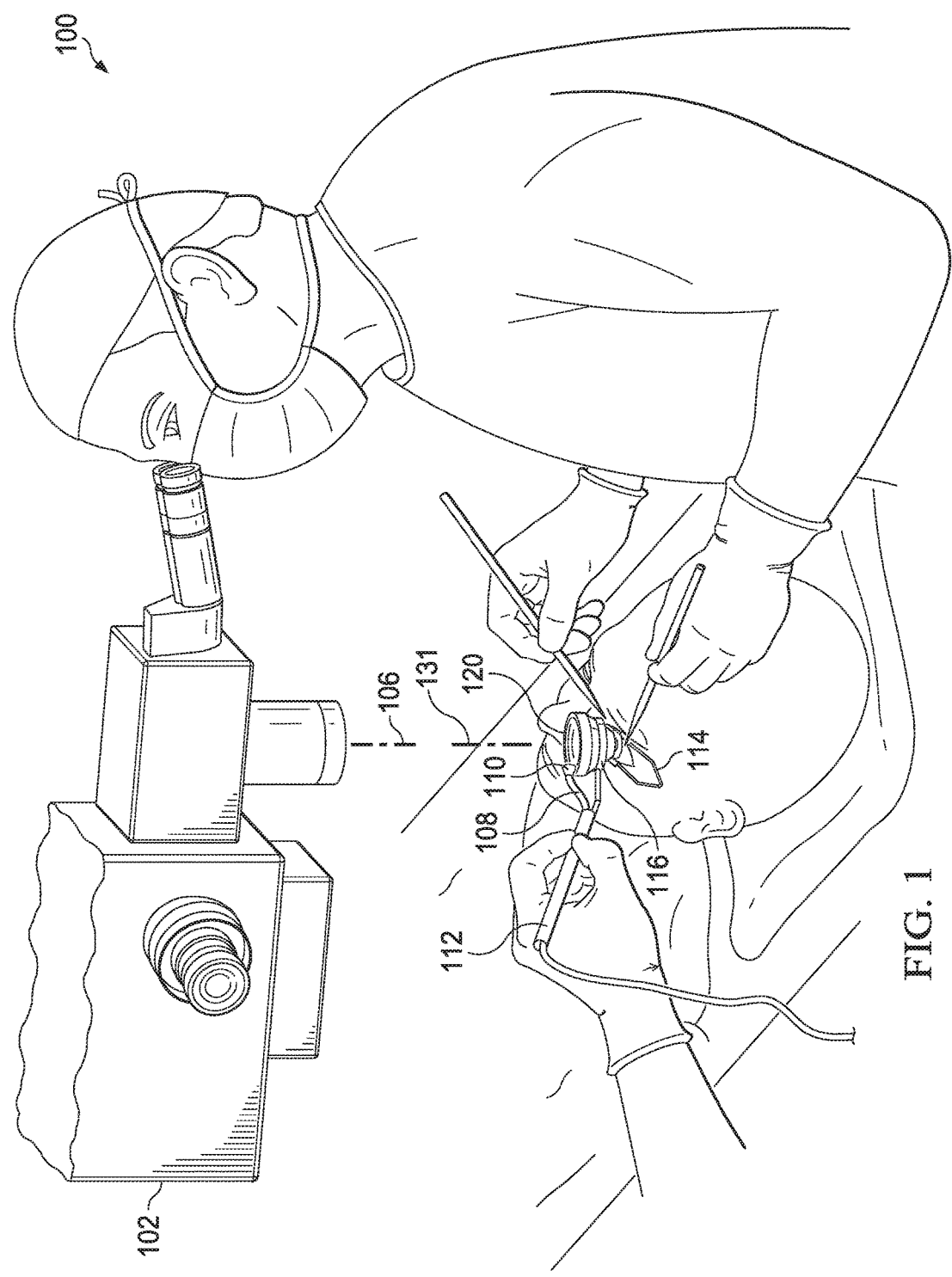
FIG. 1 is a depiction of an embodiment of an ophthalmic surgery using a surgical microscope and a contact lens with an anti-fogging device.

Referring now to the drawings, FIG. 1 illustrates a depiction of an embodiment of a ophthalmic surgery 100 using a surgical microscope 102 and contact lens 120. In FIG. 1, the use of contact lens 120 with a patient and a surgeon is depicted. Although FIG. 1 is shown with surgical microscope 102 above the patient, it is noted that different orientations of the patient with respect to surgical microscope 102 may be practiced in different embodiments. In particular embodiments, contact lens 120 may be an indirect contact lens.

The patient has an eye exposed using a speculum 114 that is in contact with contact lens 120, while the surgeon is viewing the fundus of the patient's eye using surgical microscope 102. Furthermore, a lens handle 112 is attached to contact lens 120 using a mounting clip 116 and is shown held in place by a surgical technician (or other personnel) to maintain alignment of a first optical axis 131 of contact lens 120 with a second optical axis 106 of surgical microscope 102, thereby enabling useful imaging for the surgeon to be maintained during surgery. Mounting clip 116 may be a single-use item to maintain sterility and may be disposable. It is noted that different means for supporting contact lens 120 may be used in different embodiments.

The objective used with surgical microscope 102 may have a focal length of about 175 mm to 225 mm that may focuses on a focal plane of contact lens 120. As long as contact lens 120 remains free from condensation (fogging), the surgeon may be provided with field of view of the fundus of the eye via surgical microscope 102 and may safely proceed with any of a variety of ophthalmic surgical procedures (not shown).

However, when contact lens 120 is fogged, typically at a top exterior surface of contact lens 120 exposed to ambient conditions, the optical path of surgical microscope 102 may become obstructed and the surgeon can no longer view the fundus of the eye. Such fogging may occur relatively quickly and without warning during surgery and may even occur at moments when the surgeon is applying the utmost care and skill to perform minute operations in the fundus, such as membrane peeling and manipulation, drainage of subretinal fluid, endolaser application, among others. Therefore, fogging of contact lens 120 may result in unnecessary delays and interruptions and may represent a potentially serious risk during ophthalmic surgery. As noted above, the ambient conditions in the operating room may be conducive to fogging of contact lens 120, such as humidity and low temperatures, which may vary locally at the location of contact lens 120 during surgery, resulting in unpredictable fogging behavior of contact lens 120.

As shown in ophthalmic surgery 100, contact lens 120 is equipped with an anti-fogging device that delivers thermal energy to contact lens 120. The anti-fogging device may be activated to maintain visibility through contact lens 120 when ophthalmic surgery 100 is performed.

In the embodiment depicted in FIG. 1, the anti-fogging device comprises an air duct 108 that may be coupled to, or integrated with, lens handle 112 that is attached via mounting clip 116 to contact lens 120. For example, lens handle 112 may be formed using stainless steel or polyether ether ketone (PEEK), which are materials that may be subject to autoclaving for disinfection. Specifically, air duct 108 may terminate with an air nozzle 110 that is directed to the surface of contact lens 120 from an edge of contact lens 120. Air duct 108 may direct warmed air over the flange edge of contact lens 120 to reach the optical surface of contact lens 120. An air supply system (not visible in FIG. 1) may provide pressurized air at a desired temperature and a desired humidity to air nozzle 110 via fluid coupling through air duct 108. In this manner, at least the surface of contact lens 120 may be kept above the local ambient dew point and condensation (fogging) may be prevented. It is noted that the temperature, humidity, pressure, flow rate, or a combination of such parameters of the pressurized air flowing through air nozzle 110 may be regulated to a desired value. Air nozzle 110 or air duct 108 or both may be single-use items to maintain sterility and may be disposable. Because the dew point may be relatively low, a relatively small increase in temperature relative to the ambient temperature in the operating room of ophthalmic surgery 100 may suffice for the pressurized air to be anti-fogging at the surface of contact lens 120.

In addition to the embodiment of the anti-fogging device depicted in FIG. 1, additional embodiments of the anti-fogging device may be implemented, as described below in the example implementations shown in FIGS. 2 and 3.

Figure 2:
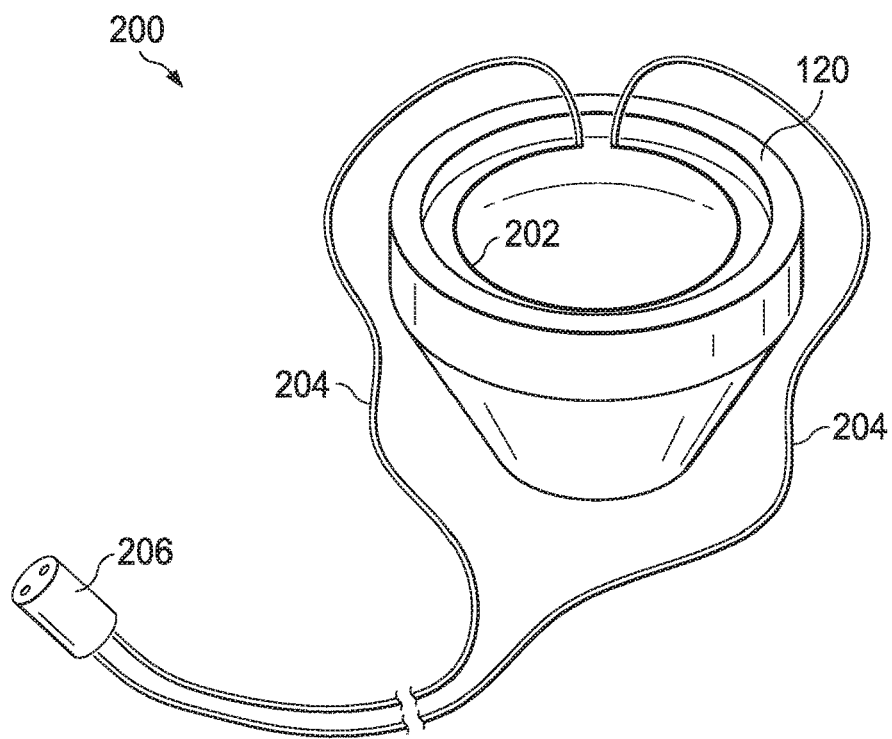
FIG. 2 is a depiction of selected embodiments of an anti-fogging device.

Referring now to FIG. 2, selected elements of an embodiment of an anti-fogging device 200 for contact lens 120 are shown. In FIG. 2, anti-fogging device 200 comprises an electrical heating element 202 shown formed as a circular ring at a peripheral portion of the surface of contact lens 120. In other embodiments, electrical heating element 202 may be placed at other positions in contact with contact lens 120, such as attached to a housing of contact lens 120, attached to a ring-shaped flange of contact lens 120, or attached to mounting clip 116 of lens handle 112. Electrical heating element 202 is coupled at both ends to lead lines 204, which may be insulated wires that are attached to an external power source (not shown) via connector 206. In various embodiments, lead lines 204 or connector 206 or both may be coupled to or integrated with lens handle 112, such that lead lines 204 are held in place using lens handle 112.

Connector 206 may be an electrical plug or an electrical socket with two poles for each respective lead line 204. When connector 206 is connected to the external power source, an electrical circuit including electrical heating element 202 is closed and current may flow through electrical heating element 202. Various different types of external power sources may be used with anti-fogging device 200, including direct current (DC) or alternating current (AC) sources. In some embodiments, the external power source is included in surgical equipment present in the operating room such that connector 206 is plugged in to the surgical equipment.

As a result of the inherent resistivity of a material used to form electrical heating element 202, electrical heating element 202 will increase in temperature when the current flows through electrical heating element 202, thereby delivering a certain amount of thermal energy to the surface of contact lens 120 to prevent condensation (fogging) from occurring at the surface.

It is noted that electrical heating element 202 may be formed using various materials. For example, a metallic material, such as a nickel-chrome (Ni—Cr) alloy, an iron-chrome-aluminum (FeCrAl) alloy, or a copper-nickel (Cu—Ni) alloy, among others, may comprise at least a portion of electrical heating element 202. In some embodiments, a transparent conductor, such as indium tin oxide (ITO), may comprise at least a portion of electrical heating element 202 in order to minimize any optical effects of introducing anti-fogging device 200 to contact lens 120. In different embodiments, electrical heating element 202 may comprise a ceramic material, such as a positive thermal coefficient (PTC) of resistance ceramic, including but not limited to barium titanate, lead titanate, and composites thereof. In some embodiments, a conductive polymer, such as a PTC rubber material, among others, may be used for electrical heating element 202. It is further noted that while a circular form is shown for electrical heating element 202 in FIG. 2, other forms or shapes may be used for electrical heating element 202.

Similar to the anti-fogging device shown in FIG. 1, it will be understood that the power output of anti-fogging device 200 may be regulated to deliver a certain amount of power, to deliver a certain amount of heat, or to maintain a certain desired temperature, or a desired temperature difference, such as with the ambient air, at contact lens 120. Accordingly, a temperature sensor may additionally be included with contact lens 120 and may be used for regulation purposes in particular embodiments. In various embodiments, a fixed amount of electrical current is continuously provided to electrical heating element 202 to provide enough thermal energy to maintain contact lens 120 at a temperature above the ambient dew point. Because the amount of thermal energy to maintain contact lens 120 at a temperature above the ambient dew point may be relatively, small, the electrical current flowing through electrical heating element 202 may be relatively small, such as a few milliamperes, depending on the dimensions and resistivity of electrical heating element 202.

Figure 3:
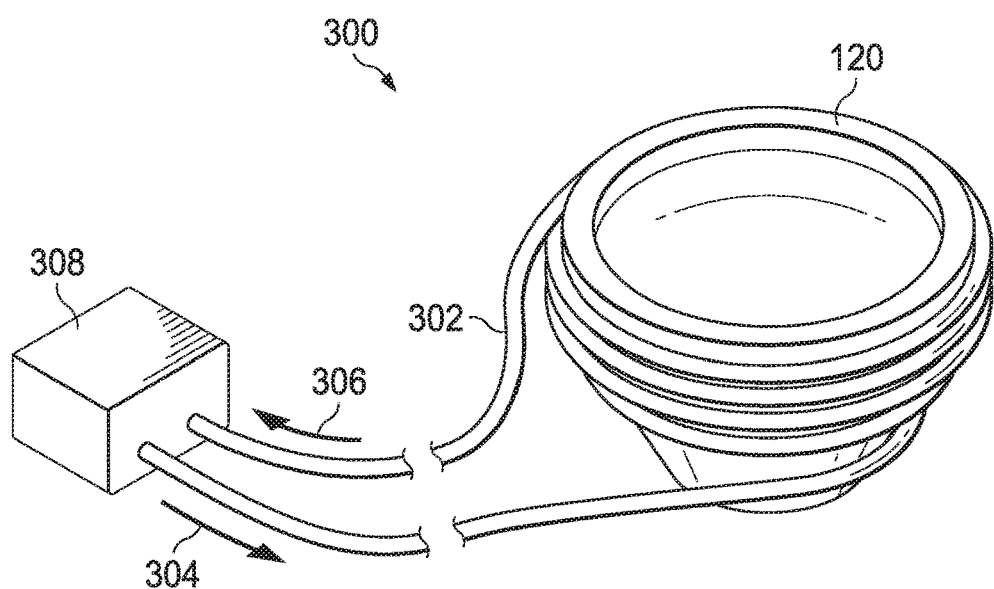
FIG. 3 is a depiction of selected embodiments of an anti-fogging device.

Referring now to FIG. 3, selected elements of an embodiment of an anti-fogging device 300 for contact lens 120 are shown. In FIG. 3, anti-fogging device 300 comprises a fluid duct 302 in thermodynamic contact with contact lens 120. In particular embodiments, fluid duct 302 may be formed comprising a thermally conductive material, such a metal tube. Anti-fogging device 300 may comprise a coil formed with fluid duct 302 that is shaped to mate with contact lens 120. In various embodiments, fluid duct 302 may be coupled to or integrated with lens handle 112, such that fluid duct 302 is held in place using lens handle 112.

As shown, a heat transfer fluid may enter fluid duct 302 from a manifold 308 in direction 304 and may exit fluid duct 302 in direction 306 to manifold 308. Manifold 308 may further include a reservoir, a heating system, and a pump system (not shown) to enable circulation of the heat transfer fluid at a desired temperature through fluid duct 302 in order to warm contact lens 120 for anti-fogging purposes. In given embodiments, the heat transfer fluid may be an aqueous solution, such as an aqueous saline solution or a sterile water solution. Similar to the anti-fogging devices shown in FIGS. 1 and 2, it will be understood that the temperature of the heat transfer fluid entering fluid duct 302 of anti-fogging device 300 may be regulated to deliver a certain amount of heat, or to maintain a certain desired temperature, or a desired temperature difference, such as with the ambient air, at contact lens 120. Accordingly, the temperature of the heat transfer fluid entering and exiting fluid duct 302 may be monitored and used for regulation purposes. In various embodiments, a fixed amount of thermal energy is continuously provided via the heat transfer fluid to fluid duct 302 to provide enough thermal energy to maintain contact lens 120 above the ambient dew point.

Figure 4:
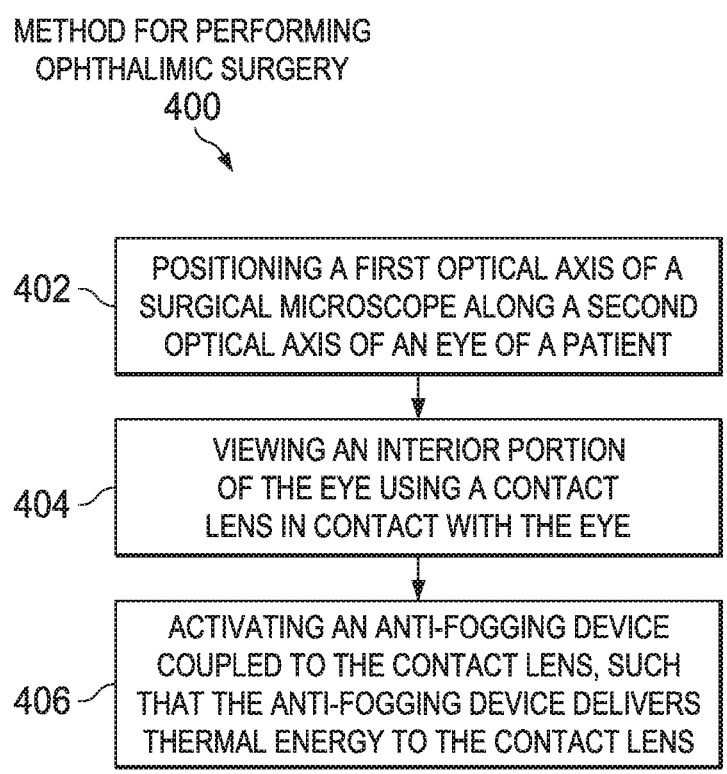
FIG. 4 is a flow chart of selected elements of a method for performing ophthalmic surgery.

Referring now to FIG. 4, a flow chart of selected elements of an embodiment of a method 400 for performing ophthalmic surgery, as described herein, is depicted in flowchart form. Method 400 describes steps and procedures for using an anti-fogging device with contact lens 120 (see FIGS. 1, 2, and 3) to view the fundus of an eye and to enable further surgical procedures based on the view of the fundus. It is noted that certain operations described in method 400 may be optional or may be rearranged in different embodiments. Method 400 may be performed by a surgeon or by other medical personnel. In some embodiments, at least certain portions of method 400 may be automated, for example using regulated control of temperature, as described above.

Method 400 may begin, at step 402, by positioning a first optical axis of a surgical microscope along a second optical axis of an eye of a patient. At step 404, an interior portion of the eye is viewed using a contact lens in contact with the eye. At step 406, an anti-fogging device coupled to the contact lens is activated, such that the anti-fogging device delivers thermal energy to the contact lens.

As disclosed herein, a contact lens for use with a surgical microscope may be equipped with an anti-fogging device to prevent obscuring the view of a surgeon due to condensation during ophthalmic surgery. The anti-fogging device may deliver thermal energy to a surface of the contact lens to heat the contact lens above an ambient dew point. The thermal energy may be delivered by an air duct with a fan nozzle, a fluid duct in thermodynamic contact with the contact lens circulating a heat transfer fluid, or generated with electrical energy to an electrical heating element disposed on the surface of the contact lens. The thermal or electrical energy may be delivered via a handle for supporting the contact lens during surgery.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for performing ophthalmic surgery, comprising:
    positioning a first optical axis of a surgical microscope along a second optical axis of an eye of a patient;
    viewing an interior portion of the eye using a contact lens in contact with the eye; and
    activating an anti-fogging device coupled to the contact lens, wherein the anti-fogging device delivers thermal energy to the contact lens.

2. The method of claim 1, wherein the anti-fogging device comprises an air duct in fluid coupling to an air nozzle directed to a surface of the contact lens, and wherein the air duct transports heated air towards the air nozzle to deliver the thermal energy.

3. The method of claim 2, wherein the air nozzle is a fan beam nozzle.

4. The method of claim 1, wherein the anti-fogging device comprises an electrical heating element disposed on a surface of the contact lens to deliver the thermal energy.

5. The method of claim 4, wherein the electrical heating element comprises a transparent conductor.

6. The method of claim 1, wherein the anti-fogging device comprises an electrical heating element disposed on a ring surrounding the contact lens.

7. The method of claim 1, wherein the anti-fogging device comprises a fluid duct in thermodynamic contact with the contact lens, and wherein the fluid duct circulates a heat transfer fluid to deliver the thermal energy.

8. The method of claim 7, wherein the heat transfer fluid is an aqueous saline or a sterile water solution.

9. The method of claim 1, wherein the anti-fogging device further comprises a handle for supporting the contact lens on the eye during surgery.

10. A contact lens for ophthalmic surgery, the contact lens comprising:
    an anti-fogging device coupled to the contact lens, wherein the anti-fogging device delivers thermal energy to the contact lens while the contact lens is in use during ophthalmic surgery to view an interior portion of an eye of a patient using a surgical microscope.

11. The contact lens of claim 10, wherein the anti-fogging device comprises an air duct in fluid coupling to an air nozzle directed to a surface of the contact lens, and wherein the air duct transports heated air towards the air nozzle to deliver the thermal energy.

12. The contact lens of claim 11, wherein the air nozzle is a fan beam nozzle.

13. The contact lens of claim 10, wherein the anti-fogging device comprises an electrical heating element disposed on a surface of the contact lens to generate the thermal energy.

14. The contact lens of claim 13, wherein the electrical heating element comprises a transparent conductor.

15. The method of claim 10, wherein the anti-fogging device comprises an electrical heating element disposed on a ring surrounding the contact lens.

16. The contact lens of claim 10, wherein the anti-fogging device comprises a fluid duct in thermodynamic contact with the contact lens, and wherein the fluid duct circulates a heat transfer fluid to deliver the thermal energy.

17. The contact lens of claim 16, wherein the heat transfer fluid is an aqueous saline or a sterile water solution.

18. The contact lens of claim 10, wherein the anti-fogging device further comprises a handle for supporting the contact lens on the eye during surgery.

19. The contact lens of claim 18, wherein the thermal energy is delivered via the handle.

20. The contact lens of claim 18, wherein electrical energy to generate the thermal energy is delivered via lead lines attached to the handle.

* * * * *